United States Patent

Chowdhury et al.

Patent Number: 5,808,117
Date of Patent: Sep. 15, 1998

[54] PROCESS FOR THE PRODUCTION OF 16-DEHYDROPREGENOLONE ACETATE FORM DIOSGENIN

[76] Inventors: Pritish Kumar Chowdhury; Manobjyoti Bordoloi; Nabin Chandra Baraua; Heramba Prasad Sarmah; Pradip Kumar Goswami; Ram Prakash Saharma; Ajoy Pratap Baruah; Raj Kumar Mathur; Anil Chandra Ghosh, all of Regional Research Laboratory, Jorhat 785006, Assam, India

[21] Appl. No.: 589,708

[22] Filed: Jan. 22, 1996

[51] Int. Cl.$^6$ ............................................. C07J 7/00
[52] U.S. Cl. ....................................................... 552/606
[58] Field of Search ............................. 549/344; 552/606

[56] References Cited

U.S. PATENT DOCUMENTS 3,136,758  6/1964  Chemerda et al. ............... 260/239.55
4,482,706  11/1984  Tomimatsu et al. .................... 536/6.1

FOREIGN PATENT DOCUMENTS 1026181C  10/1994  China .

Primary Examiner—Allen J. Robinson
Assistant Examiner—Barbara Badio
Attorney, Agent, or Firm—Peter A. Borsari

[57] ABSTRACT

The invention relates to a process for producing 16-Dehydropregnenolone acetate (16DPA) of the formula shown below

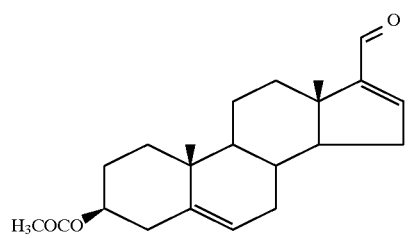

which process comprises a) acetolysis of diosgenin of the formula shown below

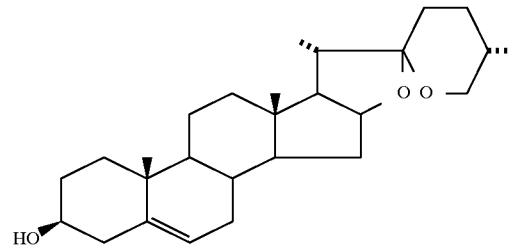

by heating in a pressure reactor in the presence of an acetylating agent and a non-polar solvent, maintaining the pressure in the reactor in the range of 4–6 kg/cm$^2$ and at a temperature in the range of 200°–250° C. to produce pseudodiosgenine acetate of the formula shown below

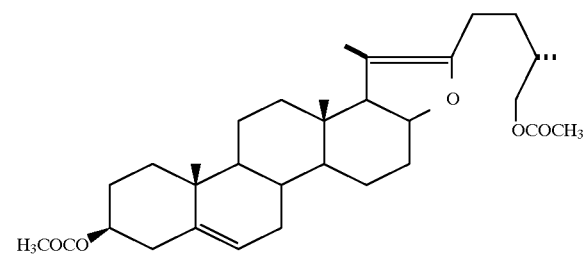

b) Oxidizing the so obtained pseudodiosgenin acetate to obtain diosone of the formula shown below

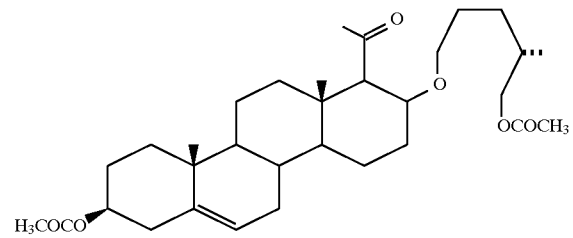

and, c) Hydrolysis and degradation of the diosone so obtained to produce the said 16-Dehydropregnenolone acetate.

17 Claims, 1 Drawing Sheet

FORMULA 1

FORMULA 2

FORMULA 3

FORMULA 4

PROCESS FOR THE PRODUCTION OF 16-DEHYDROPREGENOLONE ACETATE FORM DIOSGENIN

BACKGROUND OF THE INVENTION

This invention relates to an improved process for the production of 16-Dehydropregnenolone acetate from diosgenin. The invention, particularly, relates to an improved process for the production of 16-Dehydropregnenolone acetate (16-DPA) of the formula 4 shown in the drawing accompanying this specification, where Ac represents acetyl ($CH_3CO$) group from Diosgenin of formula 1 of the drawing. The compound of formula 4 prepared by the process of the invention is found to have a purity of 98% by GLC (gas liquid chromatography) and yield of 55–60%. The process of the present invention does not involve the use of any high boiling liquid and also does not involve use of costly and environmentally toxic catalysts. The recovery of the solvent is also possible which makes the process simple and economic. The process of the present invention has been developed using a very non-toxic, low-cost and medium boiling organic solvent under moderately high pressure.

PRIOR ART

The hitherto known processes for the preparation of pseudodiosgenin diacetate of formula 2 of the drawing where Ac represents acetyl group employ generally Marker's degradation of diosgenin of formula 1 in which diosgenin is heated for several hours (8 to 12 hr.) in a sealed vessel with acetic anhydride at an elevated temperature such as 200°–250° C. (Ref: Marker RE and Rohrman E; *J Am Chem Soc*, 61, 3592 (1939). Marker RE & Rohrman E; *ibid*, 62, 518, 1940)

The drawback of the method is found to be poor yield (50%) of pseudodiosgenin diacetate of formula 2.

Another group of workers, Dauben et al have reported a process in which diosgenin acetate is heated in acetic anhydride containing pyridine hydrochloride as catalyst which afforded pseudodiosgenin diacetate in 84% yield. (Ref:Dauben WG and Fonken GJ; *J Am Chem Soc*, 76, 4618, 1954).

Although the yield of pseudodiosgenin diacetate according to the above said process of Dauben et al is looked to be good (84%), the use of pyridine hydrochloride have severe disadvantages for making the process commercially viable. The catalyst employed i.e. pyridine hydrochloride is also toxic. The process is also costly as the catalyst could not be recovered for reuse, thereby making the process non-economical.

In a study of the degradation of a number of sapogenins at the Glaxo Laboratorties in UK, good results were obtained by heating diosgenin in refluxing n-Octanoic acid (bp 237° C.) containing acetic anhydride, distilling off the low boiling fraction until the temperature reached 270° C. and refluxing for 2 hours followed by saponifications resulting in the production of pseudodiosgenin in a yield of 87% (Ref:Cameroon AFB, Evans RM, Hamlet JC, Hunt JS, Jones PG and Long AG, *J Chem Soc*, 2807 1955.)

The drawback of the above method is the use of a very high boiling solvent like n-octanoic acid and the corrosive nature of the solvent which is not suitable for a commercial application. Further, the recovery of such high boiling solvent would be more energy intensive thereby making the process uneconomical.

Studies by Schering-New Jersey group showed that the Acetolysis of diosgenin of formula 1 to pseudodiosgenin diacetate of formula 2 catalysed by acids and lewis acids like p-tolune sulfonic acid, aluminium chloride etc. and the yield of pseudodiosgenin diacetate is reported to be 33%. (Ref: Gould DR Staeudle H and Hershberg EB; *J Am Chem Soc*, 74, 3685 1952)

Since the yield of pseudodiosgenin diacetate of formula 2 is only 33%, consequently the yield of 16-DPA prepared from the said method is also very poor.

The drawback of the above said catalytic method is that the catalysts used could not be recovered. These catalysts are toxic and also costly. The yield of pseudodiosgenin diacetate is found to be poor (33%). Under these circumstances, the process is not commercially viable.

Daniewski et al have also reported the yield of 16-DPA from diosgenin as 67% in laboratory scale using another catalytic method. The process involves the use of catalysts like Pyridinium hydrochloride and titanium tetrachloride both of which are highly toxic.

The handling of $TiCl_4$ is not feasible in large scale production of 16-DPA. Moreover these costly catalysts could not be recoverable. Therefore, they are not suitable for the commercial use of the process. (Ref: Daniewski AR and Kinowski A, *Poland patent No:*119829, 1984).

Similar types of works on this line have also been reported by the other group of workers such as Ref: Khuyen HN and Dan NV, *Tap. Chi. Hoa.Hoc.* 14(1), 37–39, 1976 and Honda KL and Rao PR, *Res. Ind.*, 15(3), 165–166, 1970. These processes also used the catalysts such as pyridinium hydrochloride. The drawbacks of the processes which have already been discussed above are also applicable to these processes.

Recently, Micovic et al have reported a process for the production of 16-DPA from diosgenin claiming an yield of 65–69% using again a catalytic method using catalyst such as pyridine. (Ref: Micovic IV, Invanovic MD and Piatak DM, *Synthesis*, 591, 1990).

The drawback of this process lies in the use of highly toxic reagents like pyridine. The catalyst used is also costly and not recoverable for reuse. Hence, the commercial exploitation of the process is not feasible although the reported yield of 16-DPA is good (65–69%).

SUMMARY OF THE INVENTION

To overcome the above difficulties and to provide an environmentally friendly process, the inventors have now evolved a process for producing 16-Dehydropregnenolone acetate (16DPA) of formula 4 shown in the drawing accompanying the specification, which comprises a) acetolysis of diosgenin of formula 1 of the drawing by heating in a pressure reactor in the presence of an acetylating agent and a non-polar solvent, maintaining the pressure in the reactor in the range of 4–6 $kg/cm^2$ and at a temperature in the range of 200°–250° C. to produce pseudodiosgenine acetate of formula 2 of the drawing; b) Oxidizing the so obtained pseudodiosgenin acetate of formula 2 to obtain diosone of formula 3; and c) Hydrolysis and degradation of the diosone of formula 3 so obtained to produce 16-Dehydropregnenolone acetate of formula 4 of the drawings accompanying the specification.

OBJECTS AND DESCRIPTION OF THE INVENTION

The main object of the present invention, therefore, is to provide a process for the preparation of 16-Dehydropregnenolone acetate of formula 4 avoiding the various drawbacks enumerated above in the hitherto known processes.

Another object of the present invention is to provide a process for the production of 16-Dehydropregnenolone acetate of formula 4 eliminating the use of expensive and environmentally toxic catalysts and to make the production of 16-DPA commercially highly feasible and economical.

Yet another object of the present invention is to provide a process for the production of 16-Dehydropregnenolone acetate of formula 4 by avoiding the use of very high boiling solvents in the process so as to avoid the recovery of such solvents which is energy intensive and consequently making the process for the commercial production of 16-DPA economical.

Still another object of the present invention is to provide a process for the production of 16-Dehydropregnenolone acetate of formula 4 from diosgenin of formula 1 having an yield of 50–60%.

Although the yield of 16-DPA prepared according to the process of the present invention looks less as compared to the hitherto known process, the simplicity of the (economically and environmentally acceptable nature) process developed by this invention makes the process commercially viable and important.

Accordingly, the present invention provides a process for the production of 16-Dehydropregnenolone acetate of formula 4 shown in the drawings accompanying this specification, which comprises a. acetolysing diosgenin of formula 1 of the drawings accompanying the specification by heating at a temperature in the range of 180°–250° C. in a pressure reactor in the presence of an acetylating agent and a non-polar solvent or a mixture thereof, maintaining the pressure in the reactor in the range of 4–6 kg/cm$^2$ to produce pseudodiosgenin diacetate of formula 2 of the drawings accompanying the specification;

b. Oxidizing the so obtained pseudodiosgenin diacetate of formula 2 by a method hereinafter described to obtain diosone of formula 3 of the drawings accompanying the specification;

c. Hydrolyzing the diosone of formula 3 shown in the drawings and as obtained above to produce 16-Dehydro-pregnenolone acetate of formula 4; and d. Separating 16-dehydropregnenolone acetate of formula 4 by conventonal methods such as crystallization, chromatography or distillation.

BRIEF DESCRIPTION OF DRAWING

For easy understanding, the reaction sequence of the process of the present invention as shown in FIG. 1.

DETAILED DESCRIPTION OF THE INVENTION

Figure 1:
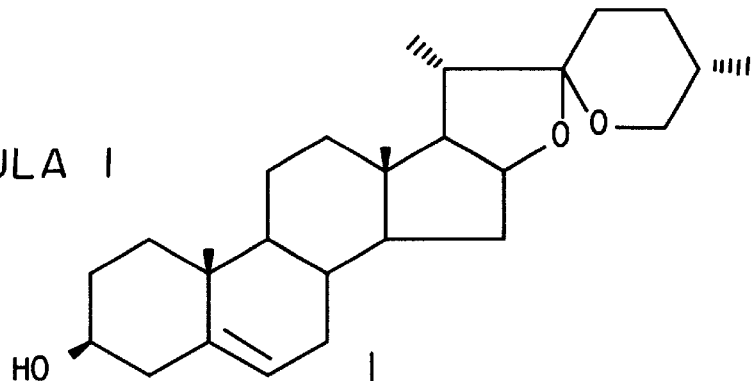
Figure 1:
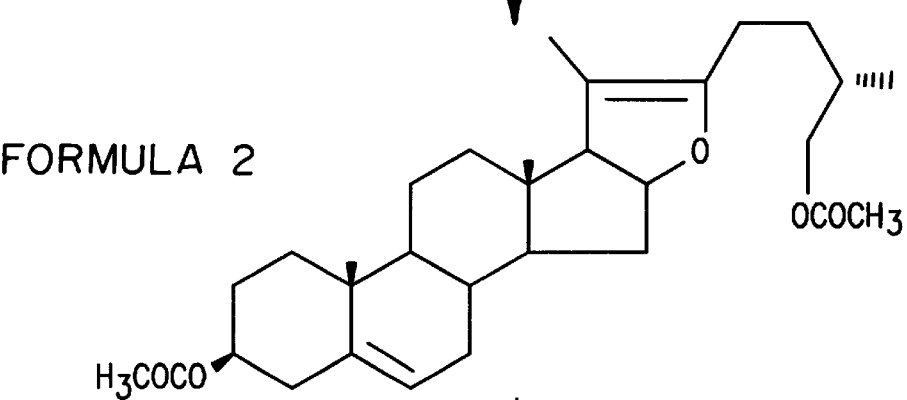
Figure 1:
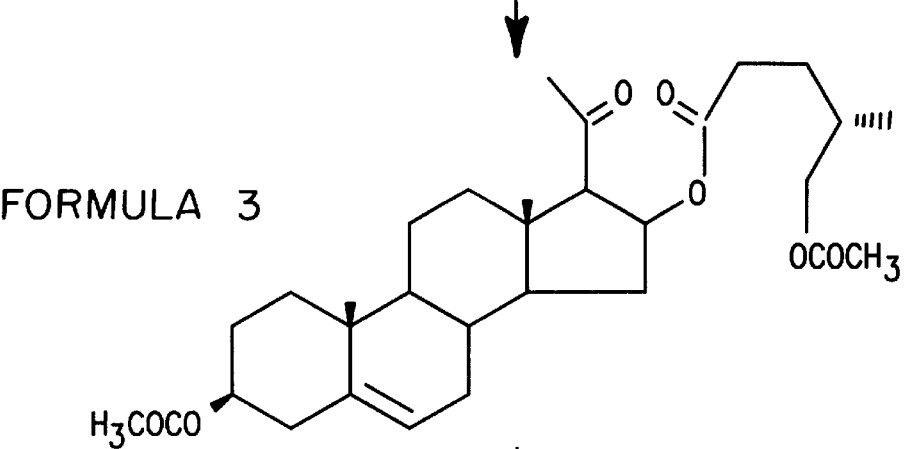
Figure 1:
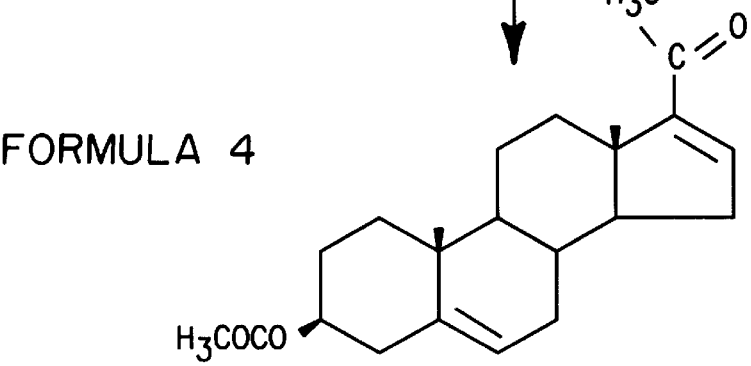

In a preferred embodiment of the present invention, the acetolysis of diosgenin can be effected using acetylating agent such as acetic anhydride, acetyl chloride, acetyl bromide. The non-polar solvent used for acetolysis reaction may be selected from toluene, benzene, xylene and aromax, mesitylene, trimethyl benzene etc or the mixtures thereof The oxidation step of the present invention can be performed by any known methods. Preferably, the oxidation of the pseudodiosgenin diacetate obtained by step (b) as stated above may be effected by using a reagent selected from chromium trioxide, pyridinium chlorochromate, pyridinium dichromate, metal (sodium, potassium etc) dichromate, potassium permanganate, hydrogen peroxide etc.

Though, the step of oxidation i.e. oxidation of pseudodiosgenin diacetate of formula 2 to obtain diosone of formula 3 can be performed in any known manner, still the applicants have now found that if the oxidation of the pseudodiosgenine diacetate obtained as explained above is carried out by applying ultra sound, preferably, at a frequency in the range of 30–40 Khz, the amount of the oxidizing agent required is found to be drastically reduced, say to about 40–60%. Furthermore, it is also observed that the oxidation reaction becomes environmentally more friendly due to the drastic reduction of the oxidizing agent required, consequently, the process also becomes economically cheaper. In other words, the oxidation of pseudodiosgenine diacetate to obtain diosone carried out under sonication (applying ultra sound) is novel and not envisaged in any of the prior art to reduce the oxidizing agent and to improve the quantity of the product in the process.

We have also observed that in the oxidation step, if water is used, preferably in the range of upto 35% by volume, more preferably in the range of 10–14% by volume, dissolution of chromium trioxide in organic acid becomes fast by approximately 30 minutes and also the oxidation process becomes smooth and there is also a substantial increase (20–30%) in the yield of the production of diosone. The temperature employed during the oxidation step may range from −10° C. to 30° C.

The oxidation procedure described above is a novel one.

The hydrolysis and degradation of the diosone of formula 3 of the accompanying drawings to produce 16-dehydropregnenolone acetate of formula 4 of the drawings are performed in any known methods.

Preferably, the hydrolysis and degradation of the diosone obtained as explained above may be effected by refluxing at a temperature in the range of 100° to 150° C. and in the presence of a base such as sodium bicarbonate, sodium carbonate, potassium carbonate, potassium bicarbonate or any similar mild base.

We have also now observed that when the diosone is hydrolyzed and degraded in the presence of a mild organic acid, the yield of 16-Dehydropregnenolone acetate is found to be higher (about 5%). Further, in this instance, it is also possible to recover the unused mild organic acids and re-use it thereby making the process economical.

The mild organic acid used may be selected from acetic acid, formic acid, propionic acid etc.

The keto ester diosone of formula 3 was extracted from the reaction mixture 1,2-dichloroethane. The organic layer after separation was subjected to distillation under reduced pressure to recover the solvent. Preferably, the distillation is performed under 700 to 100 mm Hg.

The details of the process disclosed in this invention have been described in the following specific examples which are provided only to illustrate the invention and therefore these should not be construed to limit the scope of the present invention.

EXAMPLE 1

(a) Acetolysis of diosgenin of formula 1 to pseudodiosgenin of formula 2

50 gms of diosgenin was charged with 40 ml of acetic anhydride and to it was added 150 ml of xylene in a pressure reactor vessel and heating was started while stirring till the temperature 200° C. and corresponding pressure of 5 Kg/cm$^2$ are reached. The reaction was carried for a period of 10 hours after attainment of desired temperature (190° to 200° C.). Heating was stopped and was allowed to be cooled under stirring for a period of one hour and the product was discharged at a temperature less than 100° C. through the discharge tube. TLC (thin layer chromatography) analysis of the sample was carried out which showed only one major spot on TLC plate.

Solvent removal was done in a rotary vacuum evaporator under reduced pressure (about 50 mbar). The recovered solvent was kept for recycle. After the removal of the last traces of the solvent, solid material was obtained which was confirmed to be pseudodiosgenin diacetate of formula 2.

The yield of pseudodiosgenin was found to be 92%.

(b) Oxidation of pseudodiosgenin diacetate of formula (2) to Diosone of formula (3)

(i) Preparation of the oxidant solution:

25 g of chromium trioxide ($CrO_3$) was dissolved in 25 ml of water and 10 ml of glacial acetic acid to get a clean solution which was precooled to 0° C.–5° C.

ii) Addition of oxidant solution:

Pseudodiosgenin diacetate obtained as above was dissolved in 100 ml of dichloroethane and 100 ml of glacial acetic acid and 25 ml of water. The mixture was cooled to 0°–5° C. and the oxidant solution prepared as above was added to it dropwise keeping the temperature of the reaction mixture below 5°–7° C. till the addition was over. After the addition of the oxidant solution was complete, cooling was discontinued and the temperature of the reaction medium was allowed to rise upto 15° C. and also allowed to be stirred at that temperature for a period 25 minutes. When thin layer chromatography indicated the completion of the reaction, a solution of 5 g of sodium-chloride in water (200 ml) and methanol (10 ml) were added and the stirring was continued for another 20 minutes.

(iii) Extraction of diosone

The keto ester diosone of formula 3 was extracted from the reaction mixture with 1,2-dichloroethane (4×200 ml). The organic layer after separation was subjected to distillation under reduced pressure to recover the solvent. A gummy residue of diosone was obtained which was purified by column chromatography using petroleum ether and ethyl acetate; the yield for diosone was found to be 75%.

c) Hydrolysis and degradation of diosone of formula (3) to 16-DPA of formula (4)

Diosone as obtained above was allowed to reflux in 200 ml of glacial acetic acid for a period of 5 hr. The reaction was monitored on TLC. After completion of the reaction, acetic acid was recovered by distilling under reduced pressure (50 mbar). The cooled residue was then treated with cold water (1 liter) to remove maximum amount of chromium salts present and as a result solid 16-DPA separated out which was collected by filtration.

The residue was thoroughly washed with cold water 5 times. Finally, the solid residue was subjected to exhaustive extraction with 1.5 liter of petroleum ether (b.p. 60°–80° C.) when a yellow solution of 16-DPA was obtained leaving a black residue.

The yellow solution on distillation gave crude yellow 16-Dehydropregnenolone acetate of formula 4 which was recrystallized from ethanol to get creamy white crystals. The yield of 16-DPA was found to be 60%.

EXAMPLE 2

(a) Acetolysis of diosgenin of formula 1 to pseudodiosgenin of formula 2

50 gms of diosgenin was charged with 40 ml of acetic anhydride and to it was added 150 ml of xylene in a pressure reactor vessel and heating was started while stirring till the temperature 200° C. and corresponding pressure of 5 $Kg/cm^2$ are reached. The reaction was carried for a period of 10 hours after attainment of desired temperature (190° to 200° C.). Heating was stopped and was allowed to be cooled under stirring for a period one hour and the product was discharged at a temperature less than 100° C. through the discharge tube. TLC analysis of the sample was carried out which showed only one major spot on TLC plate.

Solvent removal was done in a rotary vacuum evaporator under reduced pressure (about 50 mbar). The recovered solvent was kept for recycle. After the removal of the last traces of the solvent, solid material was obtained which was confirmed to be pseudodiosgenin diacetate of formula 2.

The yield of pseudodiosgenin was found to be 92%.

(b) Oxidation of pseudodiosgenin diacetate of formula (2) to Diosone of formula (3)

(i) Preparation of the oxidant solution:

25 g of chromium trioxide ($CrO_3$) was dissolved in 25 ml of water and 10 ml of glacial acetic acid to get a clean solution which was precooled to 0° C.–5° C.

ii) Addition of oxidant solution:

Pseudodiosgenin diacetate obtained as above was dissolved in 100 ml of dichlorethane and 100 ml of glacial acetic acid and 25 ml of water. The mixture was cooled to 0°–5° C. and the oxidant solution prepared as above was added to it dropwise keeping the temperature of the reaction mixture below 5°–7° C. till the addition was over. After the addition of the oxidant solution was complete, cooling was discontinued and the temperature of the reaction medium was allowed to rise upto 15° C. and also allowed to be stirred at that temperature for a period of 25 minutes. When thin layer chromatography indicated the completion of the reaction, a solution of 5 g of sodium chloride in water (200 ml) and methanol (10 ml) added and the stirring was continued for another 20 minutes.

iii) Extraction of diosone

The keto ester diosone of formula 3 was extracted from the reaction mixture with 1,2-dichloroethane (4×200 ml). The organic layer after separation was subjected to distillation under reduced pressure to recover the solvent. A gummy residue of diosone was obtained which was purified by column chromatography using petroleum ether and ethyl acetate; the yield for diosone was found to be 75%.

c) Hydrolysis and degradation of diosone of formula (3) to 16-DPA of formula (4)

The crude and gummy material of diosone obtained as described above was packed in a small column (1=4 ft, b=1.5 inch) of silica gel (500 gms) and was kept for 25 hours. After that the column was eluted with petroleum ether and ethyl acetate with increasing polarity. The eluent gave pure 16-DPA alongwith little amount of pure diosone for further operation leaving all the undesired chromium salts which got absorbed in the silica gel.

The solid obtained was recrystallized from ethanol to get creamy white crystals of 16-DPA of more than 98% purity by gas liquid chromatography. The yield of 16-DPA was found to be 61%.

EXAMPLE 3

(a) Acetolysis of diosgenin of formula 1 to pseudodiosgenin of formula 2

30 gms of diosgenin was charged with 25 ml of acetic anhydride and to it was added 120 ml of tolune in a pressure reactor vessel and heating was started while stirring till the temperature 200° C. and corresponding pressure of 6 $Kg/cm^2$ are reached. The reaction was carried for a period of 10 hours after attainment of desired temperature (190° to 210° C.). Heating was stopped and was allowed to be cooled under stirring for a period of one hour and the product was discharged at a temperature less than 100° C. through the discharge tube. TLC analysis of the sample was carried out which showed only one major spot on TLC plate.

Solvent removal was done in a rotary vaccum evaporator under reduced pressure (about 50 mbar). The recovered solvent was kept for recycle. After the removal of the last traces of the solvent, solid material was obtained which was confirmed to be pseudodiosgenin diacetate of formula 2.

The yield of pseudodiosgenin was found to be 80%.

(b) Oxidation of pseudodiosgenin diacetate of formula (2) to Diosone of formula (3).

(i) Preparation of the oxidant solution:

20 g of chromium trioxide ($CrO_3$) was dissolved in 10 ml of water and 20 ml of glacial acetic acid to get a clean solution which was precooled to 0° C.–5° C.

ii) Addition of oxidant solution:

Pseudodiosgenin diacetate obtained as above was dissolved in 100 ml of dichloroethane and 100 ml of glacial acetic acid and 25 ml of water. The mixture was cooled to 0°–5° C. and the oxidant solution prepared as above was added to it dropwise keeping the temperature of the reaction mixture below 5°–7° C. till the addition was over. After the addition of the oxidant solution was complete, cooling was discontinued and the temperature of the reaction medium was allowed to raise upto 15° C. and also allowed to be stirred at that temperature for a period of 25 minutes. When thin layer chromatography indicated the completion of the reaction, a solution of 5 g of sodium chloride in water (200 ml), and methanol (10 ml) were added and the stirring was continued for another 20 minutes.

iii) Extraction of diosone 3 from the reaction mixture:

The keto ester diosone of formula 3 was extracted from the reaction mixture with 1,2-dichloroethane (4×200 ml). The organic layer after separation was subjected to distillation under reduced pressure to recover the solvent. A gummy residue of diosone was obtained which was purified by column chromatography using petroleum ether and ethyl acetate; the yield for diosone obtained after purification was found to be 75%.

c) Hydrolysis and degradation of diosone of formula (3) to 16-DPA of formula (4)

Diosone as obtained above was allowed to reflux in 200 ml of glacial acetic acid for a period of 5 hr. The reaction was monitored on TLC. After completion of the reaction, acetic acid was recovered by distilling under reduced pressure (50 mbar). The cooled residue was then treated with cold water (1 liter) to remove maximum amount of chromium salts present and was a result solid 16-DPA separated out which was collected by filtration.

The residue was thoroughly washed with cold water 5 times. Finally, the solid residue was subjected to exhaustive extraction with 1.5 liter of petroleum ether (b.p. 60°–80° C.) when a yellow solution of 16-DPA was obtained leaving a black residue.

The yellow solution on distillation gave crude yellow 16-Dehydropregnenolone acetate of formula 4 which was recrystallized from ethanol to get creamy white crystals. The yield of 16-DPA was found to be 50%.

EXAMPLE 4

(a) Acetolysis of diosgenin of formula 1 to pseudodiosgenin diacetate of formula 2

50 gms of diosgenin was charged with 40 ml of acetic anhydride and to it was added 150 ml of mesitylene in a pressure reactor vessel and heating was started while stirring till the temperature 200° C. and corresponding pressure of 3–5 $Kg/cm^2$ are reached. The reaction was carried for a period of 10 hours after attainment of desired temperature (190° to 200° C.). Heating was stopped and was allowed to be cooled under stirring for a period of one hour and the product was discharged at a temperature less than 100° C. through the discharge tube. TLC analysis of the sample was carried out which showed only one major spot on thin layer chromatography (TLC) plate.

Solvent removal was done in a rotary vacuum evaporator under reduced pressure (about 50 mbar). The recovered solvent was kept for recycle. After the removal of the last traces of the solvent, solid material was obtained which was confirmed to be pseudodiosgenindiacetate of formula 2.

The yield of pseudodiosgenin was found to be 92%.

(b) Oxidation of pseudodiosgenin diacetate of formula (2) to Diosone of formula (3).

Pseudodiosgenin diacetate of formula 2 obtained as above was dissolved in 200 ml of dichloromethane. To the solution was added 30 gms of pyridinium chlorochromate while stirring at the temperature of 18° C. The stirring was continued for 4 hr. and the reaction was monitored on TLC (thin layer chromatography). When TLC indicated the completion of the reaction, 50 ml of diethyl ether was added. After that the solution was decanted off to be washed with cold water several times. Finally, the organic part was evaporated in a rotary vacuum evaporated under reduced pressure (100 mbar) to get crude diosone of formula 3 which was purified by chromatography. The yield of diosone was found to be 78%.

c) Hydrolysis and degradation of diosone of formula (3) to 16-DPA of formula (4)

Diosone obtained as above was allowed to reflux in 200 ml of glacial acetic acid for a period of 5 hr. The reaction was monitored on TLC. After completion of the reaction, acetic acid was recovered by distilling under reduced pressure (50 mbar). The cooled residue was then treated with cold water (1 liter) to remove the maximum amount of chromium salts present and as a result, solid 16-DPA separated out which was collected by filtration. The residue was throughly washed with cold water 5 times. Finally, the solid residue of 16-DPA was subjected to exhaustive extraction with 1.5 liter of petroleum ether (b.p.60°–80° C.) when a yellow solution of 16-DPA was obtained leaving a black residue.

The yellow solution on distillation under reduced pressure (50 mbar) gave crude yellow 16-Dehydropregnenolone acetate of formula 4 which was recrystallized from acetone to get creamy white crystals. The yield of 16-DPA was found to be 50%.

EXAMPLE 5

(a) Acetolysis of diosgenin of formula 1 to pseudodiosgenin diacetate of formula 2.

50 gms of diosgenin was charged with 40 ml of acetic anhydride, 75 ml of xylene and 75 ml of toluene in a pressure reactor vessel and heating was started while stirring till the temperature 200° C. and corresponding pressure of 4.4 Kg/cm2 are reached. The reaction was carried for a period of 10 hours after attainment of desired temperature (190° to 200° C.). Heating was stopped and was allowed to be cooled and stirring for a period of one hour and the product was discharged at a temperature less than 100° C. through the discharge tube. TLC analysis of the sample was carried out which showed only one major spot on TLC plate.

Solvent removal was done in a rotary vacuum evaporator under reduced pressure (about 50 mbar). The recovered solvent was kept for recycle. After the removal of the last traces of the solvent, solid material was obtained which was confirmed to be pseudodiosgenin diacetate of formula 2.

The yield of pseudodiosgenin diacetate by column chromatography was found to be 86%.

(b) Oxidation of pseudodiosgenin diacetate of formula (2) to Diosone of formula (3)

(i) Preparation of the oxidant solution:

25 g of chromium trioxide ($CrO_3$) was dissolved in 40 ml of water and 10 ml of glacial acetic acid to get a clean solution which was precooled to 0° C.–5° C.

ii) Addition of oxidant solution:

Pseudodiosgenin diacetate obtained as above was dissolved in 100 ml of dichloroethane and 100 ml of glacial acetic acid and 25 ml of water. The mixture was cooled to 0°–5° C. and the oxidant solution prepared as above was added to it dropwise keeping the temperature of the reaction mixture below 5°–7° C. till the addition was over. After the addition of the oxidant solution was complete, cooling was discontinued and the temperature of the reaction medium was allowed to rise upto 20° C. and also allowed to sbe tirred at that temperature for a period of 25 minutes. When thin layer chromatography indicated the completion of the reaction, a solution 5 g of sodium chloride in water (200 ml) and methanol (10 ml) were added and the stirring was continued for another 20 minutes.

iii) Extractiion of diosone 3 from the reaction mixture:

The keto ester diosone of formula 3 was extracted from the reaction mixture with 1,2-dichloroethane (4×200 ml). The organic payer after separation was subjected to distillation under reduced pressure to recover the solvent. A gummy residue of diosone was obtained which was purified by column chromatography using petroleum ether and ethyl acetate; the yield of diosone was found to be 75%.

c) Hydrolysis and degradation of diosone of formula (3) to 16-DPA of formula (4)

Diosone as obtained above was allowed to reflux in 200 ml of glacial -acetic acid for a period of 5 hr. The reaction was monitored on TLC. After completion of the reaction, acetic acid was recovered by distilling under reduced pressure (50 mbar). The cooled residue was then treated with cold water (1 liter) to remove the maximum amount of chromium salts present and as a result, solid 16-DPA separated out which was collected by filtration.

The residue was thoroughly washed with cold water 5 times. Finally, the solid residue was subjected to exhaustive extraction with 1.5 liter of petroleum ether (b.p. 60°–80° C.) when a yellow solution of 16-DPA was obtained leaving a black residue.

The yellow solution on distillation gave crude yellow 16-Dehydropregnenolone acetate of formula 4 which was recrystallized from ethnol to get creamy white crystals. The yield of 16-DPA was found to be 52%.

EXAMPLE 6

(a) Acetolysis of diosgenin of formula I to pseudodiosgenin of formula 2

50 gms of diosgenin was charged with 40 ml of acetic anhydride and to it was added 150 ml of xylene in a pressure reactor vesel and heating was started while stirring till the temperature 200° C. and corresponding pressure of 5 $Kg/cm^2$ are reached. The reaction was carried for a period of 10 hours after attainment of desired temperature (190° to 200° C.). Heating was stoped and was allowed to be cooled under stirring for a period of one hour and the product was discharged at a temperature less than 100° C. through the discharge tube. TLC analysis of the sample was carried out which showed only one major spot on TLC plate.

Solvent removal was done in a rotary vacuum evaporator under reduced pressure (about 50 mbar). The recovered solvent was kept for recycle. After the removal of the last traces of the solvent, solid material was obtained which was confirmed to be pseudodiosgenin diacetate of formula 2.

The yield of pseudodiosgenin was found to be 92%.

b) Oxidation of pseudodiosgenin diacetate of formula 2 to diosone of formula 3

I) Preparation of the oxidant solution.

12.5 g of chromium trioxide ($CrO_3$) was dissolved in 20 ml of water and 10 ml of glacial acetic acid to get a clean solution which was precooled to 0° C.–5° C.

B. Addition of the oxidant solution:

Pseudodiosgenin diacetate obtained as above was dissolved in 100 ml of dichloroethane and 100 ml of glacial acetic acid and 25 ml of water. The mixture was cooled to –5° to 5° C. and the oxidant solution prepared as above was added dropwise keeping the temperature of the reaction mixture below 5° C., till the addition of oxidant solution was over, over a period of 1 hr. The reaction mixture was sonicated at 35 Khz all the time beginning at the time of addition of chromium trioxide solution. After the addition of oxidant solution was complete, the mixture was allowed to remain under sonication at that temperature for a period of half an hour. When the reaction was complete as indicated by TLC, sonication was stopped and 10 ml of methanol were added and the sonication continued for another 15 minutes. The reaction mixture was diluted with a solution containing 5 g sodium chloride in 500 ml of water.

iii) Extraction of diosone of formula 3 from the reaction mixture:

The keto ester diosone of formula 3 was extracted from the reaction mixture with 1,2-dichloroethane (4×200 ml). The organic layer after separation was subjected to distillation under reduced pressure to recover the solvent. A gummy residue of diosone was obtained which was purified by column chromatography using petroleum ether and ethyl acetate; the yield for diosone was found to be 95%.

c) Hydrolysis and degradation of diosone of formula 3 to 16-DPA of formula 4.

Diosone as obtained above was allowed to reflux in 200 ml of glacial acetic acid for a period of 5 hr. The reaction was monitored on TLC. After completion of the reaction, acetic acid was recovered by distilling under reduced pressure(50 mbar). The cooled residue was then treated with cold water (1 liter) to remove maximum amount of chromium salts present and as a result solid 16-DPA separated out which was collected by filteration.

The residue was thoroughly washed with cold water 5 times. Finally, the solid residue was subjected to exhaustive extraction with 1.5 liter of petroleum ether (b.p. 60°–80° C.) when a yellow solution of 16-DPA was obtained leaving a black residue.

The yellow solution on distillation gave crude yellow 16-Dehydropregnenolone acetate of formula 4 which was recrystallized from ethanol to get creamy white crystals. The yield of 16-DPA was found to be 55–65%.

| Sl. NO. | Items | Existing process | Proposed process | Comments |
| --- | --- | --- | --- | --- |
| 1. | Raw materials used | Diosgenin, Acetic anhydride, catalyst like Pyridine hydrochloride, Titanium tetrachloride, | Diosgenin, Acetic anhydride | The method used by Glaxo and other companies is very old and based on Schering Technology of 1952 but the |

| Sl. NO. | Items | Existing process | Proposed process | Comments |
|---|---|---|---|---|
| | | Aluminium chloride etc. | | present process is developed through the technology of 1993 In the present process, acetic which is a reactant has been used not in large excess along with a solvent giving pseudodiosgenin diacetate (2). Large excess of acetic anhydride lowers the yield of the above product |
| 2. | Catalyst | | | |
| | i. Cost: | Expensive Py.HCl (about U.S. $175/Kg) TiCl$_4$ (about U.S. $150/ 10 gm) AlCl$_4$) | No catalyst has been used in the proposed process | In the present process, the use of expensive and environmentally hazardous toxic catalysts has been completely eliminated |
| | ii. Toxicity | TiCl$_4$ (Highly Toxic) Py.HCl (Toxic) AlCl$_3$ (Corrosive) | | |
| | iii. Recovery Cost: | Catalysts used are Not recoverable | | |
| 3. | Solvent used | High boiling solvent like n-Octanoic acid (bp. 237° C. Glaxo) is used | Medium boiling (bp less than 150° C. solvent has been used | In the present process no high boiling and toxic solvent like n-octanoic acid (corrosive nature) have been used as recovery of such solvent would be more energy intensive. |
| 4. | Oxidation Reaction | Oxidant in Acetic Acid Yield of Diosone (3) 55% | Oxidant in Solvent Yield of Diosone (3) 70% | The oxidation has been done in presence of a non-toxic solvent which is recoverable |
| 5. | Yield of Pseudodiosgenin diacetate (2) | 87% (using n-octanoic acid) | 92% | Yield under the present process is good. |
| 6. | Yield of 16-DPA | 42–46% (Overall) | 55–62% (Overall) | Yield in the present process is good |
| 7. | Effluent generation | Step 1: Toxic effluent | Step 1: Nil | Solvents used in the present process are recoverable and can be reused |
| | | Step II: Chromium salts | Step II: Chromium salts | In the present process the use of ultra-sound in the oxidation step reduces the amount of chromium reagent by about 50% which would minimise chromium salt in the effluent. |

We claim:

1. A process for the production of 16-Dehydropregnenolone acetate (16DPA) resented by the formula structure I:

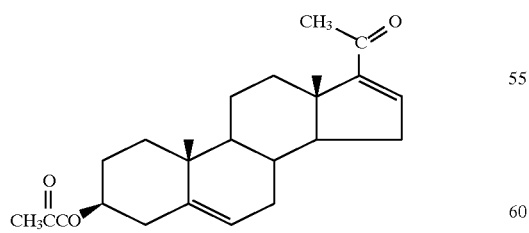

comprising the following steps:

(a) acetolyzing diosgenin represented by the formula structure II:

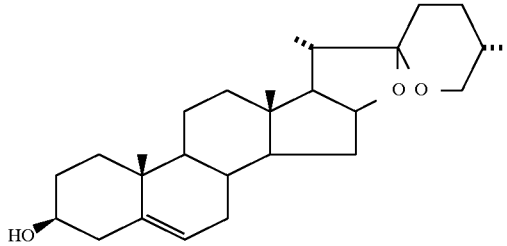

in the presence of an acetylating agent and a non-polar solvent, at an elevated temperature in the range from about 200° to about 250° C. in a pressure reactor at a pressure in the range of about 4.0 to about 6.0 kg/cm$^2$ to produce pseudodiosgenin acetate as represented by the formula structure III:

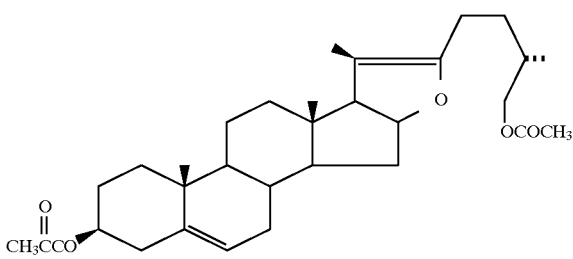

(b) oxidizing the resulting pseudodiosgenin acetate to produce diosone as represented by the formula structure IV:

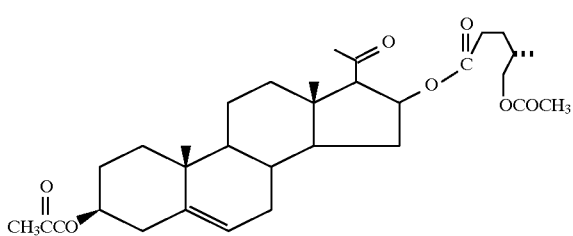

by the application of ultrasound;

(c) hydrolyzing and degrading the resulting diosone to produce 16-Dehydro-pregnenlone acetate.

2. The process in accordance with claim 1, wherein said acetylating agent is selected from group consisting of acetic anhydride, acetyl chloride or acetyl bromide.

3. The process in accordance with claim 1, wherein said non-polar solvent is selected from the group consisting of xylene, benzene, toluene trimethyl benzene, mesitylene and the mixtures thereof.

4. The process in accordance with 1, wherein said oxidation of said pseudodiosgenin acetate is effected in the presence of an oxidizing agent selected from the group consisting of chromium trioxide, pyridinium chlorochromate, pyridinium dichromate, alkali dichromate, potassium permanganate, hydrogen peroxide and mixtures thereof.

5. The process in accordance with claim 4, wherein said oxidizing agent is a mixture of chromium trioxide in acetic acid water and pyridinium, chlorochromate.

6. The process in accordance with claim 1, wherein said oxidation of said pseudodiosgenin acetate is effected by applying ultrasound in the presence of an oxidizing agent.

7. The process in accordance with claim 6, wherein said oxidizing agent is a mixture of chromium trioxide in acetic acid water and pyridinium chlorochromate.

8. The process in accordance with claim 1, wherein the frequency of the ultrasound is in the range of about 30.0 to about 40.0 Khz.

9. The process in accordance with claim 1, wherein said oxidation of said pseudodiosgenin acetate in effected in a reaction mixture containing from about 10.0 to about 14.0% water.

10. The process in accordance with claim 1, wherein the oxidation of said pseudodiosgenin acetate is effected at a temperature in the range of about −5.0° to about 20.0° C.

11. The process in accordance with claim 1, wherein said diosone is hydrolyzed and degraded by refluxing at a temperature in the range of about 100° to about 150° C. in the presence of a base selected from the group consisting of sodium carbonate, potassium carbonate and dilute sodium hydroxide solution.

12. The process in accordance with claim 1, wherein said diosone is hydrolyzed in the presence of in the presence of a mild organic acid.

13. The process in accordance with claim 12 wherein said mild organic acid is selected from the-group consisting of acetic acid, formic acid and propionic acid.

14. The process in accordance with claim 1, wherein said hydrolyzing and degradation of said diosone is effected by silica gel in a glass column.

15. The process in accordance with claim 1, wherein said produced 16-Dehydropregnenolone acetate is separated from a reaction mixture by crystallization, chromatography or distillation means.

16. A process for the production of 16-Dehydropregnenolone acetate (16DPA) represented by the formula structure I:

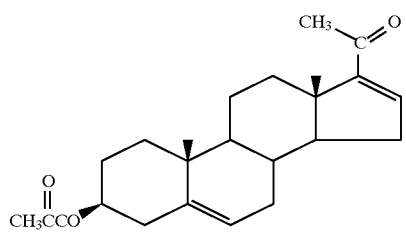

comprising the following steps:

(a) acetolyzing diosgenin represented by the formula structure II:

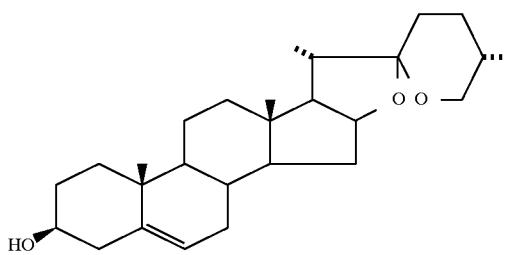

in the presence of an acetylating agent and a non-polar solvent selected from the group consisting of xylene, benzene, toluene trimethyl benzene, mesitylene and mixtures thereof at an elevated temperature in the range from about 200° to about 250° C. in a pressure reactor at a pressure in the range of about 4.0 to about 6.0 kg/cm² to produce pseudodiosgenin acetate as represented by the formula structure III:

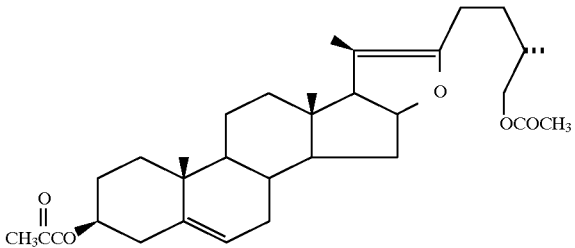

(b) oxidizing the resulting pseudodiosgenin acetate to produce diosone as represented by the formula structure IV:

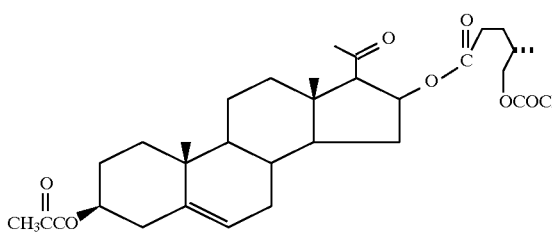
(c) hydrolyzing and degrading the resulting diosone to produce 16-Dehydropregnenlone acetate.
17. The process in accordance with claim 16, wherein said oxidation of said pseudodiosgenin acetate is effected by applying ultrasound at a frequency in the range of about 30.0 to about 40.0 Khz.
* * * * *